(12) United States Patent
Smith et al.

(10) Patent No.: US 8,152,745 B2
(45) Date of Patent: Apr. 10, 2012

(54) ACTIVITY MONITORING

(75) Inventors: Warren D. Smith, Sacramento, CA (US); Anita Bagley, Sacramento, CA (US)

(73) Assignee: Shriners Hospitals for Children, Tampa, FL (US)

( * ) Notice: Subject to any disclaimer, the term of this patent is extended or adjusted under 35 U.S.C. 154(b) by 425 days.

(21) Appl. No.: 12/392,606

(22) Filed: Feb. 25, 2009

(65) Prior Publication Data
US 2009/0221937 A1 Sep. 3, 2009

Related U.S. Application Data

(60) Provisional application No. 61/031,295, filed on Feb. 25, 2008.

(51) Int. Cl.
*A61B 5/11* (2006.01)
(52) U.S. Cl. .................................................. 600/595
(58) Field of Classification Search ................... 600/587, 600/595
See application file for complete search history.

(56) References Cited

U.S. PATENT DOCUMENTS

| | | | |
|---|---|---|---|
| 6,160,478 A | 12/2000 | Jacobsen et al. | |
| 6,433,690 B2 | 8/2002 | Petelenz et al. | |
| 6,501,386 B2 | 12/2002 | Lehrman et al. | |
| 6,819,247 B2 | 11/2004 | Birnbach et al. | |
| 7,150,048 B2 | 12/2006 | Buckman | |
| 7,177,684 B1 * | 2/2007 | Kroll et al. ...................... | 607/17 |
| 7,191,089 B2 | 3/2007 | Clifford et al. | |
| 2005/0043652 A1 * | 2/2005 | Lovett et al. .................. | 600/595 |
| 2005/0234314 A1 * | 10/2005 | Suzuki et al. ................. | 600/301 |
| 2006/0167387 A1 * | 7/2006 | Buchholz et al. ............. | 600/595 |
| 2006/0214806 A1 | 9/2006 | Clifford et al. | |
| 2006/0282021 A1 * | 12/2006 | DeVaul et al. ................ | 600/595 |
| 2007/0032748 A1 * | 2/2007 | McNeil et al. ................ | 600/595 |
| 2007/0219468 A1 * | 9/2007 | Shah et al. .................... | 600/587 |
| 2008/0133277 A1 * | 6/2008 | Jang et al. ......................... | 705/3 |
| 2009/0069724 A1 * | 3/2009 | Otto et al. ..................... | 600/595 |
| 2009/0247910 A1 * | 10/2009 | Klapper ........................ | 600/595 |
| 2010/0033422 A1 * | 2/2010 | Mucignat et al. ............ | 345/156 |
| 2010/0076692 A1 * | 3/2010 | Vock et al. ...................... | 702/19 |
| 2010/0121226 A1 * | 5/2010 | Ten Kate et al. ............. | 600/595 |
| 2010/0137748 A1 * | 6/2010 | Sone et al. .................... | 600/595 |
| 2010/0152623 A1 * | 6/2010 | Williams ...................... | 600/595 |

FOREIGN PATENT DOCUMENTS

WO  WO 2007138930 A1 * 12/2007

OTHER PUBLICATIONS

Doughty, K. et al. "The Design of a Practical and Reliable Fall Detector for Community and Institutional Telecare." *Journal of Telemedicine and Telecare*, vol. 6, Supplement 1, pp. S150-S154, 2000.

(Continued)

*Primary Examiner* — Max Hindenburg
*Assistant Examiner* — Michael C Stout
(74) *Attorney, Agent, or Firm* — Fish & Richardson P.C.

(57) ABSTRACT

Sensors and methods for automatically detecting and recording physical activities of an individual are described. An event is detected, in which data representative of at least one physical activity of an individual is received from an activity monitor associated with the individual. The data is combined into at least two intermediate calculations. A score is generated from the at least two intermediate calculations. The score is compared to a predefined threshold to decide whether or not an event has occurred. Data representative of the event is recorded.

33 Claims, 9 Drawing Sheets

OTHER PUBLICATIONS

Mathie, Merryn J. et al. "Accelerometry: providing an integrated, practical method for long-term, ambulatory monitoring of human movement." *Physiological Measurement*, vol. 25, pp. R1-R20, 2004.

Mathie, Merryn J. et al. "A pilot study of long-term monitoring of human movements in the home using accelerometry." *Journal of Telemedicine and Telecare*, vol. 10, pp. 144-151, 2004.

Miyauchi, Kosuke et al. "A New Microcomputer-Based Safety and Life Support System for Solitary-Living Elderly People." *Biomedical Sciences Instrumentation*, vol. 39, pp. 179-182, 2003.

Wilson, L.S. et al. "Building the Hospital Without Walls- a CSIRO Home Telecare Initiative." *Telemedicine Journal*, vol. 6, No. 2, pp. 275-281, 2000.

* cited by examiner

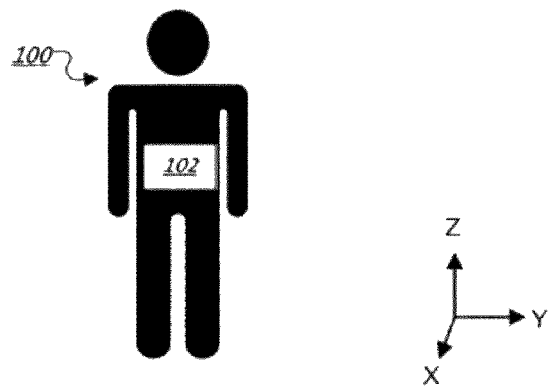
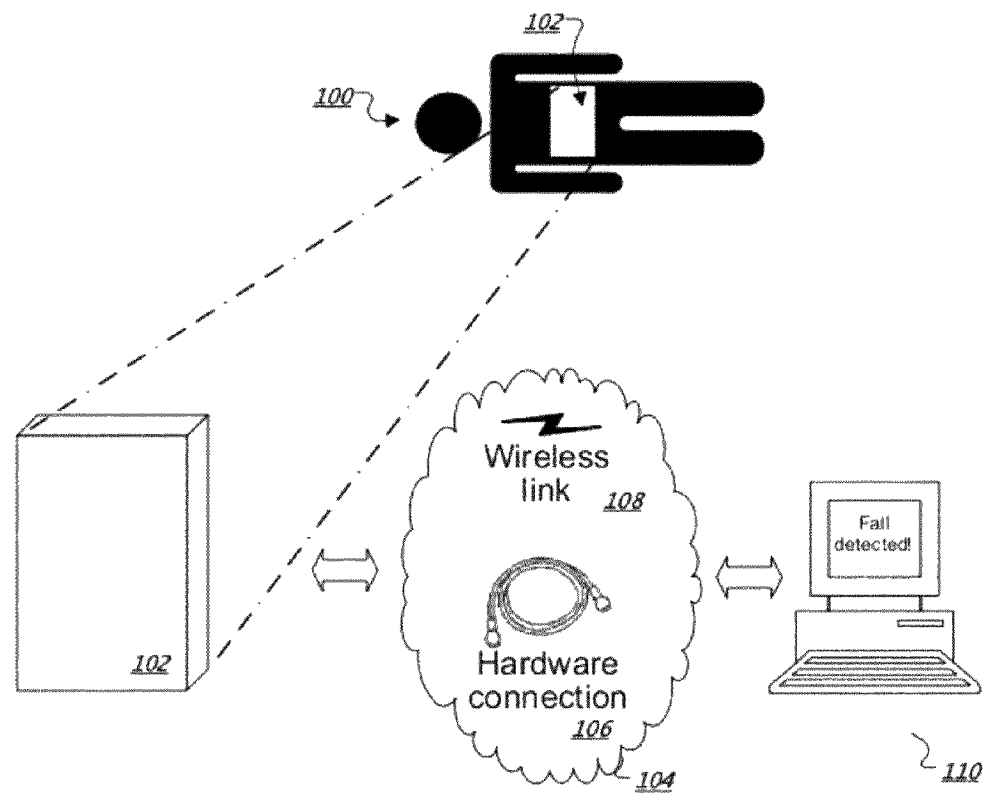

ACTIVITY MONITORING

This application claims priority to U.S. provisional application No. 61/031,295, titled "Activity Monitoring," filed on Feb. 25, 2008, the entire contents of which are incorporated herein by reference.

TECHNICAL FIELD

This disclosure relates to sensing and recording the position and motion of a person and, more particularly, to a device for measuring the activity of an individual and identifying an event such as a fall.

BACKGROUND

Monitoring patients provides doctors and care givers information to assess the patient well-being and the treatment efficacy. For example, one can monitor a patient's internal vital signs (e.g., blood pressure, heartbeat) by employing devices, such as sphygmomanometers, stethoscopes, or electrocardiographs, to retrieve relevant information. One can also assess the state of a patient by recording external information, such as food and drug intake, sleep duration, etc.

By monitoring the motion of a subject's arm, leg, torso, head, or other body part, information may be gathered to gain an understanding of the subject's respective kinematics in health, in chronic or acute illness, and after treatment.

SUMMARY

The devices, systems, and techniques described herein relate to sensors and methods for automatically detecting and recording physical activities of an individual. For example, a device called an activity monitor is attached to an individual (e.g., it is worn by the person) and is used to collect and to process data to determine whether or not an event, such as a fall, has occurred. For example, this activity monitor uses sensors to monitor quantities, such as acceleration along one or more axes, and executes operations to calculate more than one quantity from the measured data. Next, the activity monitor combines these quantities into a figure of merit and compares this value against a predetermined threshold to automatically detect events. This predetermined threshold is based on prior observations of at least three subjects who are wearing the activity monitor.

The techniques and methodologies associated with these operations are unique and robust, allowing the activity monitor to evaluate subjects while they are performing a range of activities, such as walking, running, jumping, tripping, and falling. Clinicians can use data obtained from the activity monitor to study various types of statistics, such as how many times per day the wearer trips or falls. This knowledge can aid clinicians to gauge the efficacy and longevity of treatment methods for disorders, such as gait disorders.

In general, in one aspect, the invention features methods of monitoring an activity, in which data representative of at least one physical activity of an individual is received from an activity monitor associated with, e.g., in contact with, the individual. The data is combined into at least two intermediate calculations. A score is generated from the at least two intermediate calculations. The score is recorded as representative of the activity.

In another aspect, the invention features an apparatus that includes at least one sensor used for sensing data related to a physical activity. A collector receives the sensed data and combines the data into at least two intermediate calculations. A detector receives the intermediate calculations. A processor is programmed to compute a score.

In another aspect, the invention features a computer program product encoded on a computer-readable medium that is operable to cause a data processing apparatus to perform operations. An operation can include receiving data representative of at least one physical activity of an individual from an activity monitor in contact with the individual. An operation can include combining the data into at least two intermediate calculations. An operation can include generating a score from at least two intermediate calculations. An operation can include recording the score as representative of the activity.

Implementations of the method, the apparatus, and the computer program product may include one or more of the following features. The data representative of the at least one physical activity is recorded. One of the at least two intermediate calculations is associated with an orientational feature of the physical activity. The data is combined and the score is generated on the activity monitor. The data is combined and the score is generated on a computer system in communication with the activity monitor. The computer system communicates with the activity monitor through a wireless communication. The score is compared to a predefined threshold to identify the occurrence of an event; and recording the score as representative of the event. The data is received from at least one sensor comprising an accelerometer. The one of the at least two intermediate calculations is associated with an activity level of the individual. Combining includes multiplying the at least two intermediate calculations. The threshold is determined by a database of measured data from at least three subjects. The event is a fall. The measurement is performed remotely. The measure of the orientational feature includes a rotational feature. The measure of the activity level includes a delayed, smoothed, squared norm of an acceleration vector. The acceleration vector is smoothed over a period of 1 minute.

Implementations may include one or more of the following features. The score is compared to a predetermined threshold to determine whether or not an event has occurred. The score is recorded as representative of the event. The data is received from at least one sensor. The sensor is an accelerometer. The combined data includes a measure of orientation multiplied by a delayed, smoothed, squared norm of the acceleration vector. The threshold is derived from a database of measured data. The sensor is located remotely from the apparatus.

Implementations may include one or more of the following features. An operation can include comparing the score to a predefined threshold to decide whether or not an event has occurred. An operation can include recording data representative of the event. The data is received from at least one sensor. The sensor is an accelerometer. The combined data includes a measure of orientation multiplied by a delayed, smoothed, squared norm of the acceleration vector. The threshold is determined by a database of measured data. The processor is further programmed to receive the data from a remote sensor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic of an individual wearing an activity monitor.

FIG. 1B is a schematic of an exemplary system for monitoring physical activity of an individual.

Like reference symbols in the various drawings indicate like elements.

DETAILED DESCRIPTION

Figure 2:
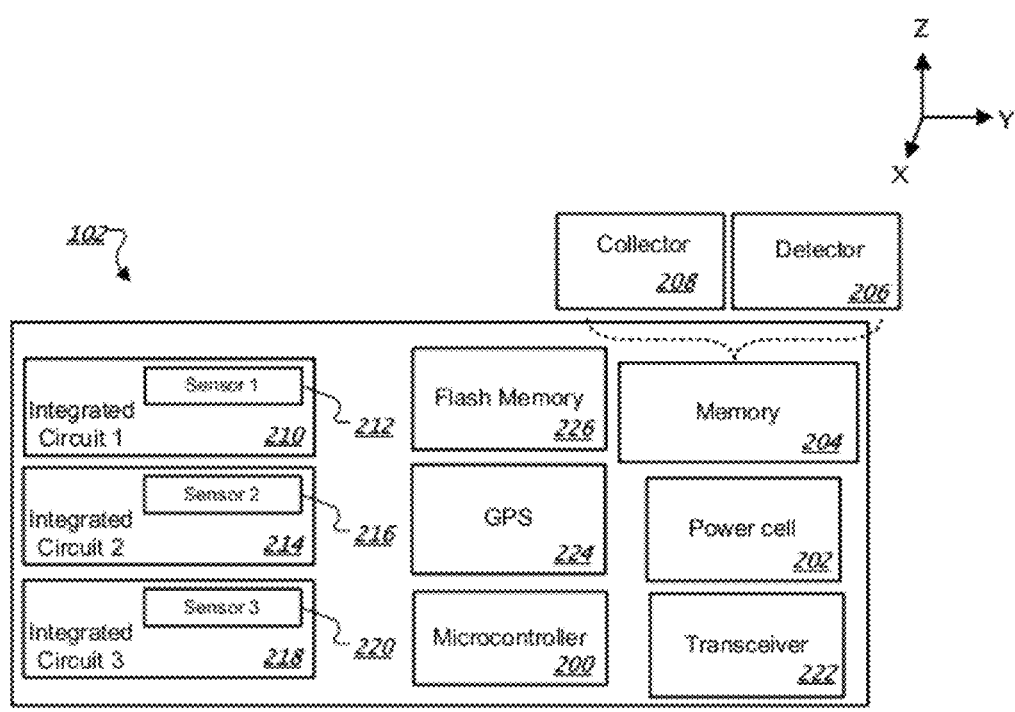
FIG. 2 is a block diagram of an exemplary activity monitor.

FIG. 1A shows an individual 100 (e.g., a person or an animal) wearing an activity monitor 102 that is capable of conveniently and accurately recording data associated with the physical activity of the individual. Generally, the activity monitor 102 is small in size, robust, and user-friendly so that clinicians can carry out data collection and analysis with relative ease. The activity monitor 102 provides data and information for various studies, e.g., to assess the efficacy of treatments for kinematic abnormalities. In this particular illustration, the individual 100 is in an upright position and the activity monitor 102 is located at waist-level (e.g., fastened using a belt) on the individual 100. The activity monitor 102 can be positioned at other locations in contact with the individual 100. For example, the activity monitor 102 can be worn on the wrist, ankle, hip, knee, elbow, neck, head, or other location. In some embodiments, the activity monitor 102 can be attached to skin, clothing, head gear (e.g., a helmet or hat), or other surface or article of clothing associated with the individual 100. For establishing spatial position, various types of coordinate systems may be used, for example, spatial axes (i.e., x, y, and z) of a rectangular coordinate system may be implemented.

FIG. 1B shows the individual 100 in a post fall position. The activity monitor 102 can detect the fall and initiate a transmission of the event to a computer system 110. This transmission can occur through a connection 104, which can be provided by a wireless link 108, a hardwire connection 106, or other transmission technique or methodology (e.g., a combination of wireless and hardwire connections).

Along with transmitting representative data, the activity monitor 102 may provide other functionality. For example, the activity monitor 102 can store a log of time-stamped events and details relevant to the monitored physical activity. Similar to the collected data, the stored data can be transferred to a computer system 110 (e.g., at a later time).

Additional communication systems and components can also be implemented for data transmission. For example, one or more local and/or global networks (e.g., local area networks (LANs), the Internet) can be implemented to assist in transferring data relevant to the event. In some implementations, multiple types of similar or different storage devices (e.g., hard drives, CD-ROMs, a redundant array of independent disks (RAID)) can be used by the computer system 110 to store data relevant to an event detected by the activity monitor 102.

Construction of Activity Monitor

FIG. 2 shows one example of the activity monitor 102, which uses acceleration sensing to aid in detecting falls of an individual. In this arrangement, the activity monitor includes three sensors (212, 216, and 220) that are each part of an integrated circuit (IC) (210, 214, and 218, respectively) and are each capable of sensing acceleration. For example, these sensors could be accelerometers packaged individually or in combination as single-axis, dual-axis, or triple-axis type, such as accelerometers manufactured by Analog Devices of Cambridge, Mass. In some embodiments, the activity monitor 102 can be enclosed in a case, for example, a plastic case (e.g., produced from shrink tubing or silicone). The case can be light in weight and can provide protections to the sensitive components of the activity monitor 102.

Outputs from such sensors can be combined to provide information relative to multiple spatial axes. For example, a tri-axial accelerometer can be formed by combining the outputs of two dual-axis accelerometers. In one arrangement, all three accelerometers of the activity monitor 102 are produced from a combination of two dual-axial accelerometers. Each of the dual-axial accelerometers 212, 216 includes two sensors having their spatial axes orthogonally arranged. For example, one sensor of the accelerometer 212 can be associated with one axis (e.g., spatial axis x), while the other sensor of the accelerometer 212 is associated with an orthogonal axis (e.g., spatial axis y). Additionally, one of the two sensors (of the second dual-axial accelerometer) may be aligned to a spatial axis (e.g., the spatial axis z) that is orthogonal to the spatial axes (e.g., the x and y axes) of the sensors (of the first dual-axial accelerometer). In some embodiments, one of the four sensors of the two dual-axial accelerometers provides a redundant spatial axis. The redundant spatial axis can provide extra data for a robust measurement. The output of the dual-axis type and the outputs of accelerometer 212 and accelerometer 216 are combined. IC 218 could be omitted or could be used to provide redundant measurements. In another arrangement, each accelerometer in FIG. 2 is of the single-axis type and the outputs of accelerometer 212, accelerometer 216, and accelerometer 220 are combined.

For embodiments in which data is obtained from three, orthogonal spatial axes, accelerometer axes can be calibrated to align along a vertical axis (e.g., represented by the z axis in FIG. 2), a right-to-left axis of the wearer (e.g., represented by the y axis), and a front-to-back axis of the wearer (e.g., represented by the x axis).

One or more electrical (e.g., circuit design) and mechanical (e.g., packaging) techniques can be used to incorporate the sensors into the activity monitor 102. For example, the three sensors can be implemented in dedicated IC's, or, two or more of the sensors may be implemented with a common IC. Similarly, one or more ICs can be used for sensor implementation. In this particular arrangement, IC 210 includes sensor 212, IC 214 includes sensor 216, and IC 218 includes sensor 220. Rather than being distributed singularly, the sensors (e.g., accelerometers) can be incorporated into multiple ICs or other types of electronic components and devices.

Some implementations of the activity monitor 102 may include a microcontroller 200, such as an MSP430 class, ultra-low power microcontroller produced by Texas Instruments of Dallas, Tex. In the proffered example, the microcontroller 200 processes data associated with detected physical activities by executing operations, functions, and the like. For example, the microcontroller 200 may include a microprocessor that processes data from the sensors 212, 216, and 220, and stores the processed data in a memory 204, which can include random access memory (RAM), dynamic RAM (DRAM), static RAM (SRAM), etc. In some implementations, the memory 204 can include one or more storage devices (e.g., hard drives), individually or in combination with memory, for storing measurement data, processes, and other types of information. In some implementations, data is stored in a flash memory 226 (e.g., a Secure Digital card, a MultiMediaCard) and can be transferred at a later time. The flash memory 226 can also store computer programs.

In some embodiments, the microcontroller 200 executes operations associated with a collector 208 and a detector 206. The collector 208, which can reside in the memory 204, provides operations for managing the collection of data from the sensor(s). In some arrangements, the collector 208 may process (e.g., preprocess, condition, etc.) the data provided by the sensors 212, 216, and 220. The detector 206, which may also reside in the memory 204, may provide operations (executable by the microcontroller 200) to process the data provided by the collector 208. For example, the detector 206 may provide operations for identifying the occurrence of one or more physical activity (e.g., a fall) associated with the wearer of the activity monitor 102.

Along with processing data on-board the activity monitor, the collected data may be processed off board (e.g., remote from the activity monitor). For example, processing instructions can be stored and executed remotely by the computer system 110. To allow such remote processing, sensor data may be transferred from the activity monitor 102 to the computer system. One or more hardwire and wireless communication techniques can be used for data transfer between the monitor 102 and the computer system 110. For example, wireless communication can be provided with a transceiver 222 (e.g., a radio frequency (RF) transceiver) or additional types of short-range communication systems, such as Bluetooth, wireless fidelity (WiFi), infrared system, etc., which can be implemented individually or in combination. In addition, a global positioning system (GPS) receiver 224 can be implemented for providing position information of the activity monitor 102 and used by applications executed on the activity monitor (e.g., by the microcontroller 200).

One or more types of sources may be implemented for providing power to the activity monitor 102. For example, The energy source of the activity monitor 102 may be a power cell 202 (e.g., a disposable battery or a rechargeable lithium-ion cell), such as the CGA103450A battery available from Panasonic of Secaucus, N.J. Other types of power sources local to the activity monitor 102 (e.g., solar cells,) or remote (e.g., power supply with hardwire connection) can be used individually or in combination.

In some embodiments, the activity monitor 102 can have the processing instruction stored on board to perform a partial or a substantially complete analysis of the sensor data. The activity monitor 102 can use an on-board rechargeable cell for power supply. As such, a charger could be attached to the monitor to recharge the cell and provide a long performance time. Once processed, data representative of the analysis can be transferred (e.g., via wireless communication techniques) to the computer system 110 for additional processing. In some embodiments, the activity monitor 102 can process the sensor data on board and also deliver the data to the computer system 110 for processing in parallel or independently. For example, by executing similar processing techniques on board (the activity monitor) and off board, various calibration techniques may be used (e.g., to adjust the design of the activity monitor).

The activity monitor 102 can include at least one connector, e.g., multi-pin connector, for various applications, for example, downloading the processing instructions prior to the use of the monitor, attaching the charger for the rechargeable cell, and downloading results from the monitor to other devices, such as the computer system 110. In some embodiments, different applications share one connector. In other embodiments, each application uses one connector.

One or more other types of functionality may also be incorporated into the activity monitor 102. For example, additional information and data may be collected. In one arrangement, a global positioning system (GPS) receiver 224 is incorporated into the activity monitor 102 (e.g., to provide a global reference to the collected data).

Figure 3:
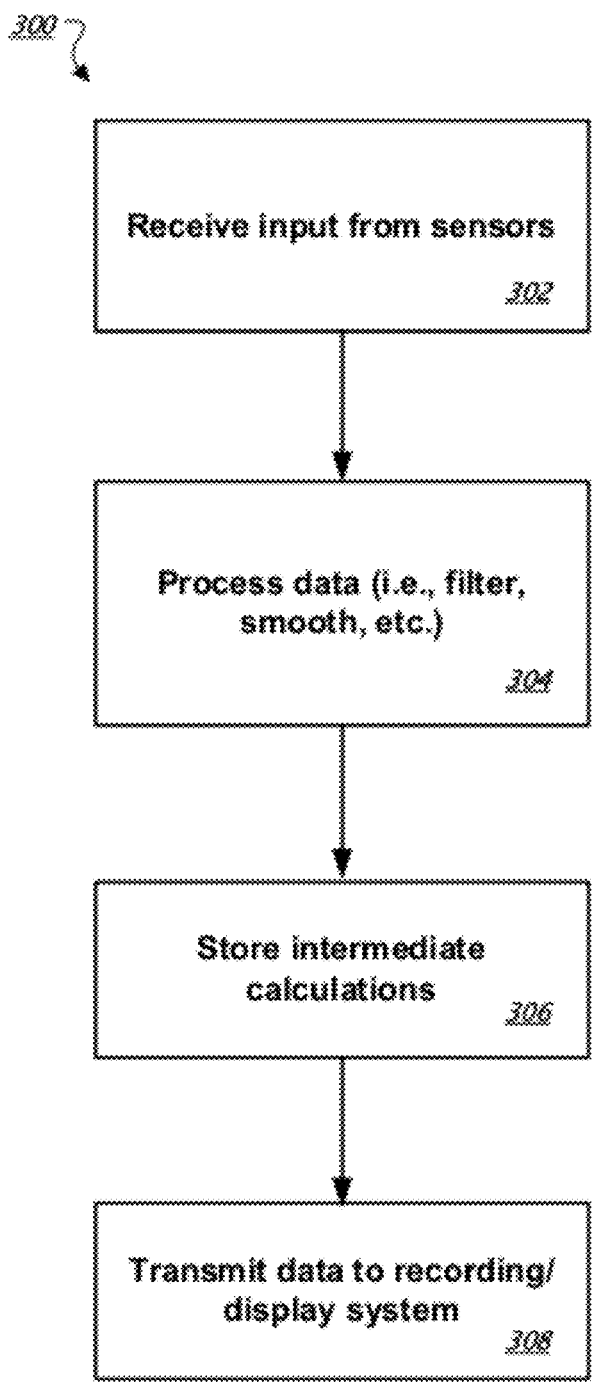
FIG. 3 is a flowchart that represents exemplary operations of a data collector.

FIG. 3 shows a flowchart 300 that represents a particular sequence of operations performed by the data collector 208. Generally, the data collector 208 manages the collection of output signals from sensors and may condition the signals for the processing provided by the detector 206. Typically the operations are executed by the microcontroller 200, which may include one or more processors. Along with centralizing processors within the microcontroller 200, processors distributed (e.g., among the activity monitor 102 and the computer system 110) may be used to execute operations. In some embodiments, operations can include receiving 302 input from the sensors included in the activity monitor. For example, signals (e.g., voltage, current, etc.) representative of the acceleration sensed by the accelerometers may be received. Operations may also include processing 304 (e.g., low-pass filtering, peak detection) the received data to produce intermediate calculations. For example, conditioning operations (e.g., low-pass filtering, etc.), initial detection (e.g., peak detection) and similar processing may be executed. Operations may also include storing 306 data representative of the intermediate calculations (e.g., in on-board memory, off-board memory, etc.). Operations may also include transmitting 308 data (e.g., collected data, processed data) for processing to identify detected fall of the individual. For example, data may be provided to the detector 206 from the collector 208. Data transmission may also provide data from the activity monitor 102 to locations (e.g., the computer system 110) for displaying, recording, and/or other processes or combination of processes.

Upon receiving data from the collector 208, the detector 206 can process the received data (e.g., intermediate calculations) to identify and to count the occurrence of detected events (e.g., falls). For example, the detector 206 can use one or more techniques and methodologies to combine intermediate calculations (from the collector 208) to produce a score.

In one arrangement, for an activity monitor that implements three orthogonally oriented sensors (e.g., accelerometers), a score can be produced as a function of time by combining the data as follows:

$$\text{score}(t) = O(t) * A(t), \quad (1)$$

where $$O(t) = (S(a_x(t), t_1)^2 + S(a_y(t), t_1)^2 + [1 - S(a_z(t), t_1)]^2), \quad (2)$$

and $$A(t)S(a_x(t-t_2)^2 + a_y(t-t_2)^2 + a_z(t-t_2)^2, t_3). \quad (3)$$

In the above equations, $a_x(t)$ represents an output signal of the first sensor at a time t, $a_y(t)$ represents an output signal of the second sensor at a time t, and $a_z(t)$ represents an output signal of the third sensor. $S(m, t_n)$ denotes a smoothing function that smoothes an input m over a time window $t_n$. The duration of smoothing time windows $t_1$ and $t_3$ can range between zero seconds and much longer durations (e.g., 5 minutes, an hour, a day, a week). The duration of the delay $t_2$ can range between zero seconds and a few (e.g., 1, 2, 5) seconds. For example, $t_1$ can range from 0.5 to 2 seconds, $t_2$ can range from 0 to 1 second, and $t_3$ can range from 0 to 0.5 seconds. In some embodiments, $t_3$ can equal 30 seconds, 1 minute, 3 minutes, 5 minutes, 15 minutes or other similar period of time.

In some embodiments, the quantity O(t) represents an orientation of individual 100 and the quantity A(t) represents a delayed, squared norm of the acceleration vector that has been smoothed over a time window $t_3$. The score represents an activity level of the individual being sensed and can be a measure of the occurrence and the severity of an event (e.g., a fall). In some embodiments, each accelerometer is positioned along an axis to form an orthogonal coordinate system (e.g., three axes represented by the x, y, and z axes of the coordinate system shown in FIG. 1), and the score can be computed by multiplying the orientation measure O(t) by a squared norm of the acceleration vector that has been delayed by a time $t_2$ and smoothed over a time window represented by $t_3$.

Without wishing to be bound by theory, the $a_x$ and $a_y$ terms on the right-hand side of equation (2) may not contribute substantial orientation information beyond the information being provided by the $a_z$ term. In some embodiments, the orientation of the individual 100 can be indicated using:

$$O'(t) = [1 - S(a_z(t), t_1)]. \quad (4)$$

Based on the orientation measure O'(t), for the situation that the individual 100 is upright, $S(a_z(t), t_1)$ is 1 and O'(t) is 0. For the situation that the individual 100 is horizontal, $S(a_z(t), t_1)$ is 0 and O'(t) is 1, and when the individual 100 is in an inverted position (e.g., upside down), $S(a_z(t), t_1)$ is −1 and O'(t) is 2. The value of O'(t) changes continuously from 0 to 2 when the orientation of the individual deviates from upright to horizontal, and finally to upside down. In some embodiments, to reduce the chance of false fall detections, O'(t) is limited to 1 when its value exceeds 1. The orientation measure can therefore be expressed as:

$$O'(t) = [1 - S(a_z(t), t_1)] \text{ if } S(a_z(t), t_1) >= 0, \quad (5)$$
$$= 1 \text{ if } S(a_z(t), t_1) < 0.$$

In some embodiments, a comprehensive orientation measure O''(t) includes the orientation measure O'(t) and a rotation feature term R(t) expressed as:

$$O''(t) = O'(t) * R(t); \quad (6)$$

in which $$R(t) = [S(a_x(t), t_4) - S(a_x(t-t_5), t_4)]^2 + \quad (7)$$
$$[S(a_y(t), t_4) - S(a_y(t-t_5), t_4)]^2 +$$
$$[S(a_z(t), t_4) - S(a_z(t-t_5), t_4)]^2$$
$$\text{if } [S(a_z(t), t_4) - S(a_z(t-t_5), t_4)] < 0, =$$
$$[S(a_x(t), t_4) - S(a_x(t-t_5), t_4)]^2 +$$
$$[S(a_y(t), t_4) - S(a_y(t-t_5), t_4)]^2$$
$$\text{if } [S(a_z(t), t_4) - S(a_z(t-t_5), t_4)] >= 0;$$

where $t_4$ denotes the time window of smoothing (e.g., 1 second) and $t_5$ denotes a delay duration (e.g., 1 second). In order to further reduce the chance of false fall detection, the term $[S(a_z(t), t_4) - S(a_z(t-t_5), t_4)]$ is set to 0 when the individual rises toward upright.

The rotation feature R(t) increases above 0 if a change in orientation has occurred recently (e.g., within the last second) and otherwise remains 0. Without wishing to be bound by theory, the rotation feature R(t) may facilitate removing false fall detection from the comprehensive orientation measure O''(t). For example, when the individual 100, e.g., a child, is deviated from upright for a long time, e.g., is in a lying position, and receives an external force (e.g., from a sibling that pounces on the child), the force can cause an impact to the activity monitor. However, due to the rotation feature R(t), the impact may not be falsely detected as a fall.

The quantity A(t) contains acceleration values $a_x$, $a_y$, and $a_z$ that each includes gravity and motion/impact components. In some embodiments, a filter (e.g., a high-pass filter) is applied to the acceleration values to remove the gravity components. By removing such contributions of the gravity components resulting in filtered accelerations $a'_x$, $a'_y$, and $a'_z$, the quantity A(t) may reduce the probability of false fall detection. The new quantity A'(t) can be expressed as:

$$A'(t) = S(a'_x(t-t_2)^2 + a'_y(t-t_2)^2 + a'_z(t-t_2)^2, t_3). \quad (8)$$

Accordingly, the score(t) of equation (1) can be represented as:

$$\text{score}'(t) = O''(t) * A'(t). \quad (9)$$

In some embodiments, the data used for calculating the score for the activity level is updated at an interval, for example, of every 1 minute, 5 minutes, or 15 minutes. Each update can include averaging all data, for example, the acceleration values, obtained from the data collector 208 during the interval. A score is calculated at the end of each interval, for example, during a total test time of two weeks and stored for further analysis. In particular, the monitor 102 that partially or completely analyzes the data from the data collector 208 includes a large storage space for storing the analyzed results for a long period of time.

In some implementations, intermediate calculations can be further processed using one or more processes such as methods of blind signal separation or feature extraction (e.g., independent component analysis, principal components analysis). Once processed, the data may be used as inputs to learning paradigms (e.g., neural networks) for decision making.

Derivation of a Threshold for Automatic Detection

By collecting sensor signals and processing sensor signals to detect events, the activity monitor 102 can calculate a score associated with the physical activity of individual 100. In some embodiments, the operations of the activity monitor 102 can use information derived from accelerometer signals about the wearer's body orientation, velocity, and acceleration to calculate a score. In one arrangement, to automatically distinguish between trips or falls and other activities, this calculated score is compared to a previously-determined threshold.

One or more thresholds for event detection can be derived by observing one or more subjects wearing activity monitors and from their activities evaluated. For example, different thresholds can be set to detect events (e.g., falls) of differing severity. Also, an appropriate selection of subjects for the observation group allows the resulting one or more thresholds to be well-matched to the sample population. For example, to detect when a sample population of motor-impaired children fall (e.g., children with cerebral palsy), processing operations and thresholds can be developed by videotaping activities of children with cerebral palsy who are wearing activity monitors. These children can be requested to perform everyday activities as well as standardized activities, such as lying down, sitting, slow walking, and fast walking. In addition, the children can be requested to perform non-fall activities, such as jumping, bumping into objects or people, being hit by a ball or other object or person, throwing a ball, or kicking a ball, that can result in accelerometer recordings similar to those for falls.

The output signals from each of three accelerometers can be recorded and processed. During data review, investigators can replay selected portions of signals versus time or examine selected windows of data with scrolling and zooming options. The record and review capabilities can assist the development of processing steps to score activity levels. These scores, accompanied by the knowledge of whether or not a fall actually occurred, then can be used to set thresholds to automatically detect subsequent trips and falls. The scoring functions can be chosen so that a score is relatively high for a fall activity (a "positive") and relatively low for a non-fall activity (a "negative"). In some embodiments, the decision threshold can be set so that as many as possible scores for fall activities lie above the threshold and as many as possible of the scores for non-fall activities lie below the threshold. For a given threshold, a score for a fall activity that lies below the threshold is called a "false negative," and a score for a non-fall activity that lies above the threshold a "false positive." In some embodiments, the threshold can be set so that the number of false negatives equals the number of false positives, so that the number of detected fall activities equals the actual number of fall activities.

Figure 4:
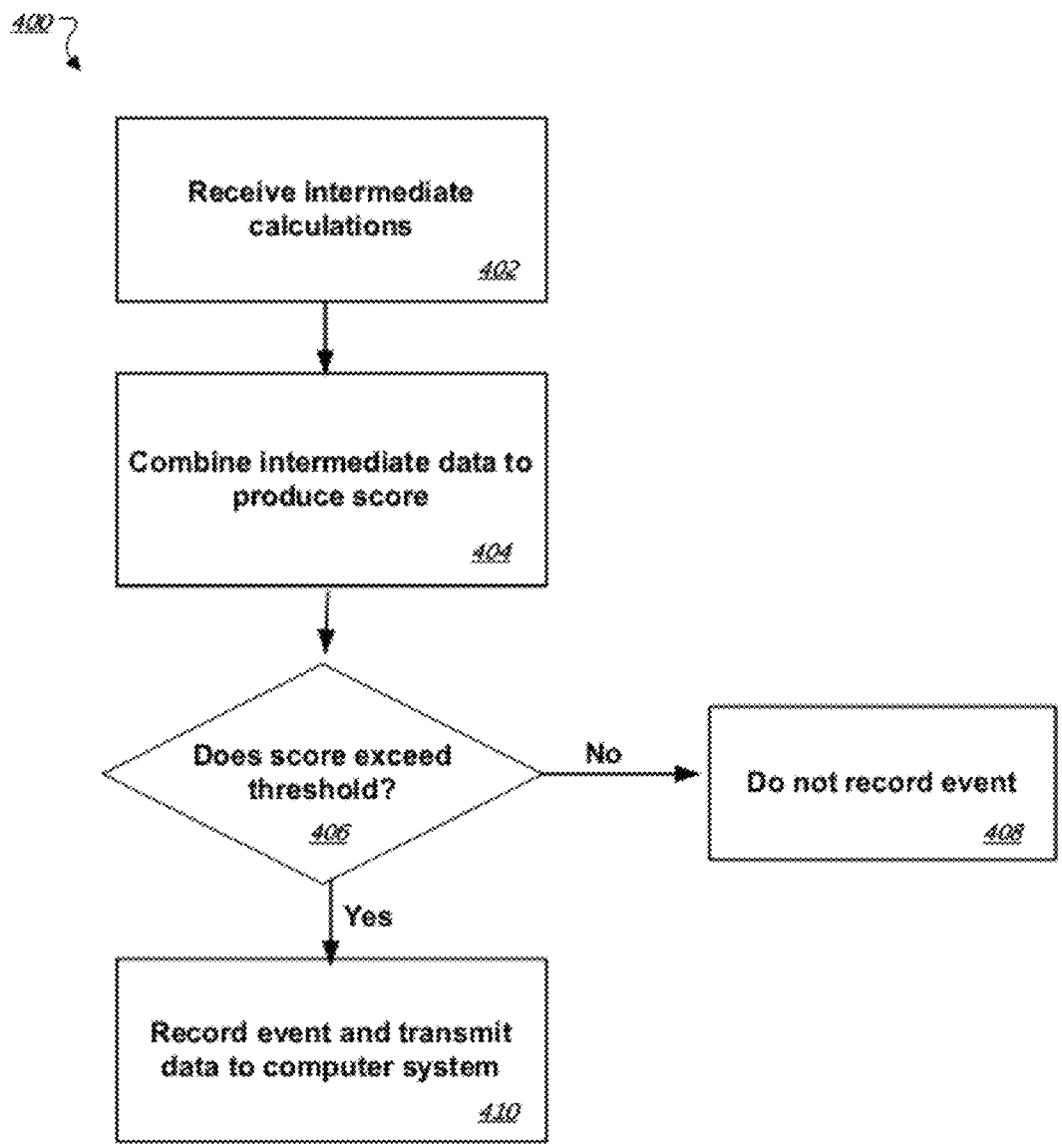
FIG. 4 is a flowchart that represents exemplary operations of a detector.

FIG. 4 shows a flowchart 400 that represents an arrangement of operations that may be provided, for example, by the detector 206. Typically the operations are executed by the microcontroller 200. However, other types of processor-based architecture may be implemented. In some embodiments, processing instructions are stored and executed remotely on the computer system 110, and sensor data is transferred from the activity monitor 102 for processing by the computer system. As such, the operations may be executed by one or multiple processors included in the computer system 110. In some embodiments, partial analysis can be performed on the activity monitor 102 and then transferred to the computer system 110 for additional processing. Operations may include receiving 402 (e.g., from the collector 208) intermediate calculations, for example, data processed by the collector 208 may be received. Operations may also include combining 404 the intermediate calculations to produce a score. Once produced, the score can be compared 406 to a pre-determined threshold to determine if a predefined event has occurred. For example, if the score exceeds that threshold, operation may include recording 410 an event. Alternatively, if the threshold is not exceeded by the score, an event may not be recorded 408. In some embodiments, receiving the intermediate calculations can include receiving the data directly from the collector 208, or can include retrieving the data from a memory (e.g., memory 204, flash memory 226, etc.) or a storage device.

Processing by the Activity Monitor

Figure 5A:
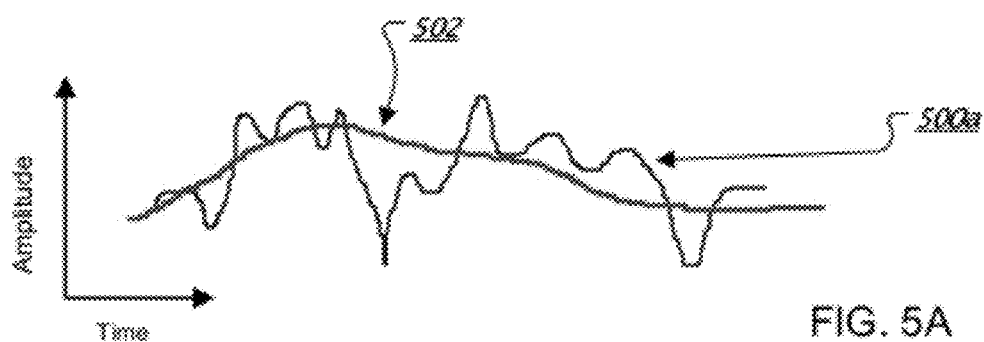
FIG. 5A is a chart that illustrates processing performed by a data collector.
Figure 5B:
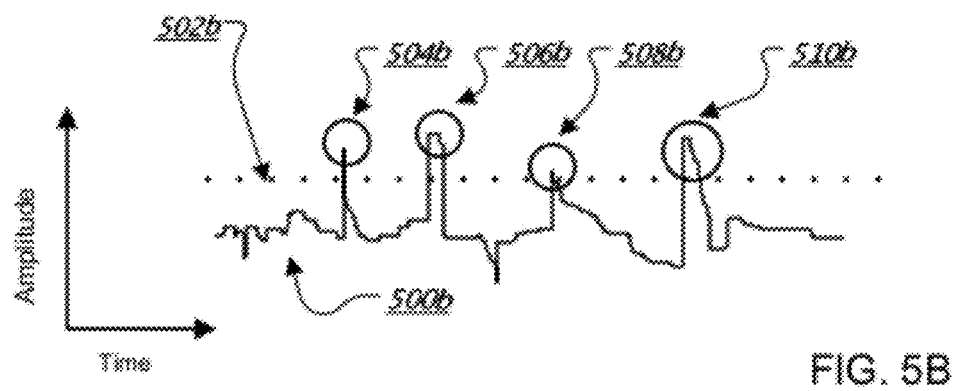
FIGS. 5B-5C are charts that illustrate processing performed by a data detector.
Figure 5C:
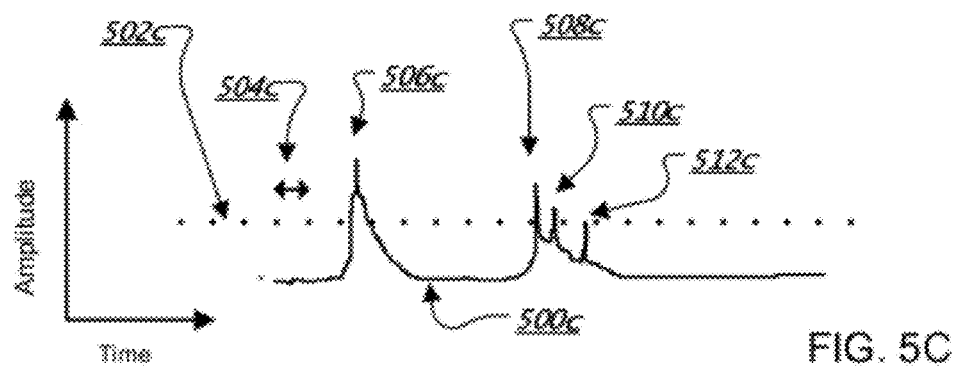

FIGS. 5A-5C show a series of charts that display data representative of one or more types of processing (e.g., analog-to-digital converting, adding, multiplying, filtering, smoothing, convolving, detecting features such as peaks or zero-crossings) performed on data received from the sensor(s) 212, 216, 220 (e.g., accelerometers).

The chart in FIG. 5A illustrates processing that can be performed by the collector 208 to produce an intermediate calculation, such as the orientation of an individual 100 wearing activity monitor 102. For example, processing the data received from sensors (e.g., accelerometers) can indicate that the individual 100 has changed from an upright to a more horizontal position. Specifically, an output signal (e.g., voltage signal) of one of the accelerometers (e.g., sensor 212) can be provided to the collector 208. As illustrated in the chart, a trace 500a represents the amplitude of the accelerometer output signal as a function of time. The trace 500a can represent acceleration (e.g., changes in the wearer's velocity) along a particular axis. Along with sensing the acceleration of the wearer, acceleration such as the Earth's gravitational acceleration (e.g., along the z direction) may be detected.

In this example, the amplitude of the trace 500a changes relatively rapidly (e.g., on a timescale of milliseconds), while a change in orientation occurs relatively slowly over time (e.g., on a timescale of seconds). A trace 502 represents the low-pass filtered signal that can be used to determine the orientation of individual 500. If, for example, the Earth's gravitational acceleration were no longer detected, the individual 100 may have changed from an upright position to a more horizontal position. This change may accompany a fall or a non-fall event, and additional information may be needed to identify the type of event that has occurred.

Along with measuring a slowly-occurring event, such as a change in an individual's orientation, relatively abrupt events can also be detected from one or more of the accelerometers. Additional sensor measurements can help ascertain whether the orientation of individual 100 has changed because of an involuntary event (e.g., a fall or trip) or because of other circumstances, such as a voluntary physical activity (e.g., the individual 100 has bent over to pick up an item). In some embodiments in which the sensors are accelerometers oriented along the x, y, and z axes, sudden accelerations that accompany falls can be measured and recorded.

Charts in FIGS. 5B and 5C illustrate processing that can be performed by the detector 206. For example, processing, shown in FIG. 5B, can be performed to detect when a trace 500b, which represents a computed score as a function of time, exceeds a predefined threshold (as represented with a dotted line 502b). The threshold can be determined based on previous measurement data. When the amplitude of trace 500b exceeds threshold (illustrated with line 502b), the time and amplitude of the event can be recorded. For example, peaks 504b, 506b, 508b, and 510b each exceed the threshold and can be recorded as "detected events" of individual 100. In addition to recording the time and amplitude of peaks that correspond to events, a log can be created that stores the amplitude and time pairs of trace 500b for a duration of time (e.g., 5 minutes, 2 hours, 1 day, 1 week).

Similarly, the chart in FIG. 5C illustrates event detection by determining when a trace 500c, which represents a score computed as a function of time, exceeds a threshold represented with a dotted line 502c. Although the temporal resolution of the trace 500c can be on the order of milliseconds, multiple occurrences of some events (e.g., falls) are not likely to occur on this timescale. After a first event is detected by the detector 206, a refractory period 504c (e.g., 1 second) can be defined during which the detector is unresponsive to a second event. For example, a part of the trace 500c, identified as peak 506c, exceeds the threshold (represented by line 502c) for many adjacent sampled points. The refractory period 504c can be chosen to equal, for example, a spacing between adjacent dots on the dotted line. Two events can be detected if each event exceeds the threshold and if the two events do not occur within one refractory period. In FIG. 5C, the detector 206 using the refractory period 506c can distinguish peaks 506c, 508c, and 512c as separate events but may not distinguish peak 510c.

In some embodiments, event detection can be accomplished by performing the described operations in different orders. Furthermore, additional operations may be included for collecting and processing data.

Methods of Using Activity Monitors

The activity monitor 102 can be attached to an individual (e.g., individual 100), e.g., using various methods and techniques (e.g., hook-and-loop fasteners, buttons, snaps, zippers, and belts) for monitoring and recording physical activities. For example, a clinician can initiate a recording session by connecting the activity monitor 102 to a computer system 110 and registering the subject by entering subject and study information. Next, the clinician can calibrate each sensor in the activity monitor 102 by first aligning a sensor axis parallel to the direction of the gravitational force of the Earth and making a measurement, which corresponds to 1 g, or 9.8 m/s$^2$ (the acceleration caused by the Earth's gravity). Next, the clinician aligns the same sensor antiparallel to the direction of the gravitational force of the Earth and makes a measurement. In this orientation, the signal corresponds to −1 g. These measurements can be used to compute offset and gain factors to convert future sensor measurements into g units. For example, when the x axis of the activity monitor is parallel to the direction of the Earth's gravitational force, the measured value can be 2108 (corresponding to 1 g), and when the activity monitor is turned over so that the x axis is now anti-parallel to the direction of the Earth's gravitational force, the measured value can be 1956 (corresponding to −1 g). To convert future measured values along the x axis into g units, an offset of (2108+1956)/2=2032 can first be subtracted from the measured values and then a gain of 2/(2108−1956)= 0.0132 can be multiplied. To calibrate all sensors in the activity monitor, the clinician could repeat these measurements for each sensor.

In some embodiments, the clinician can check the calibration of the activity monitor using software on a computer system (e.g., the computer system 110). A clinician can recalibrate an activity monitor as necessary. The clinician can be prompted to orient the activity monitor sequentially in the parallel and anti-parallel orientations for each sensor (e.g., six positions for three sensors). After this sequence of measurements, the software can automatically compute offset and gains for each axis and download these calibration values into the flash memory 226 of the activity monitor for use during monitoring sessions.

In some embodiments, the activity monitor 102 can be calibrated remotely by sending commands and data to the RF transceiver 222. The activity monitor 102 can be connected to the computer system 110 via a wireless link 108 or via a hardware connection 106. After the registration and calibration is completed, the activity monitor 102 can be disconnected from the computer system 110 and attached to the individual 100 to be monitored. In some embodiments, the activity monitor 102 can be prepared for operation after being positioned on the person of the individual. At the completion of the recording session, or at any time during the recording session, the activity monitor 102 can be reconnected to the computer system 110 (e.g., by the hardwire connection, the wireless connection) and data can be transferred for processing by the computer system 110 or another computing device.

A computer system 110 supporting the use of the activity monitor 102 could be programmed using a data-collection software with a graphical user interface, e.g., LabVIEW® software, which is commercially available from National Instruments of Austin, Tex. This software package allows the activity monitor 102 to operate as a virtual instrument with a graphical user interface. The virtual instrument permits clinicians to manage the interactions with the activity monitor 102 at the beginning and end of recording sessions and can graphically and numerically display and analyze the uploaded activity data.

Implementation

Implementation of the subject matter and the functional operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a computer readable medium for execution by or to control the operation of a data processing apparatus.

The computer-readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to a suitable receiver apparatus.

A computer program (often referred to as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical, or optical disks. However, a computer need not have such devices.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user, as well; for example, feedback provided to the user can be any form of sensory feedback, e.g., visual feedback, auditory feedback, or tactile feedback; and input from the user can be received in any form, including acoustic, speech, or tactile input.

EXAMPLES

The activity monitors and methods of use are further described in the following examples, which do not limit the scope of what is described in the claims.

The first example illustrates how a threshold is determined from the observation of at least 3 (i.e., 72) subjects. The second example shows how the derived threshold from Example 1 can be applied to a large set of children.

Example 1

Determining a Fall Threshold for an Activity Monitor

Processing operations and thresholds were developed to detect when children diagnosed with cerebral palsy fall by videotaping activities of a total of 72 children wearing activity monitors. Twenty eight of these children had been diagnosed with cerebral palsy and the remaining 44 were control subjects.

Children who had been diagnosed with cerebral palsy played together with control children in small groups (e.g., four children). The groups were videotaped during a session, lasting about 15 minutes, in which at least three cameras were used to ensure that at least one camera captured a good view of each child at all times. Typically, three sessions were recorded, with breaks in between, for a total of about 45 minutes of recordings per child. Each camera recorded a video for the three sessions sequentially, using the same videotape (e.g., a MiniDV tape). Typically, accelerometer signals were simultaneously monitored from four of the children in the group.

Each accelerometer recording and videotape recording was reviewed in its entirety. Videotapes were transferred to a DVD disk to facilitate viewing and analysis. While viewing the video recordings, logs of the times of occurrence and descriptions of fall activities as well as non-fall activities for each child were created. For each of the fall activities and the non-fall activities identified on video, plots of the corresponding calibrated accelerometer recordings were visually examined over time windows of varying lengths, ranging from about a few seconds to about 15 minutes. It was determined heuristically that about 20 seconds is a good window length to observe the nature of the accelerometer waveforms before, during, and after a fall activity. By examining the collection of recordings, similarities from fall to fall were visually identified, as well as differences between fall activities and non-fall activities. These observations led to the development of the employed method for automatic detection described previously.

Figure 6:
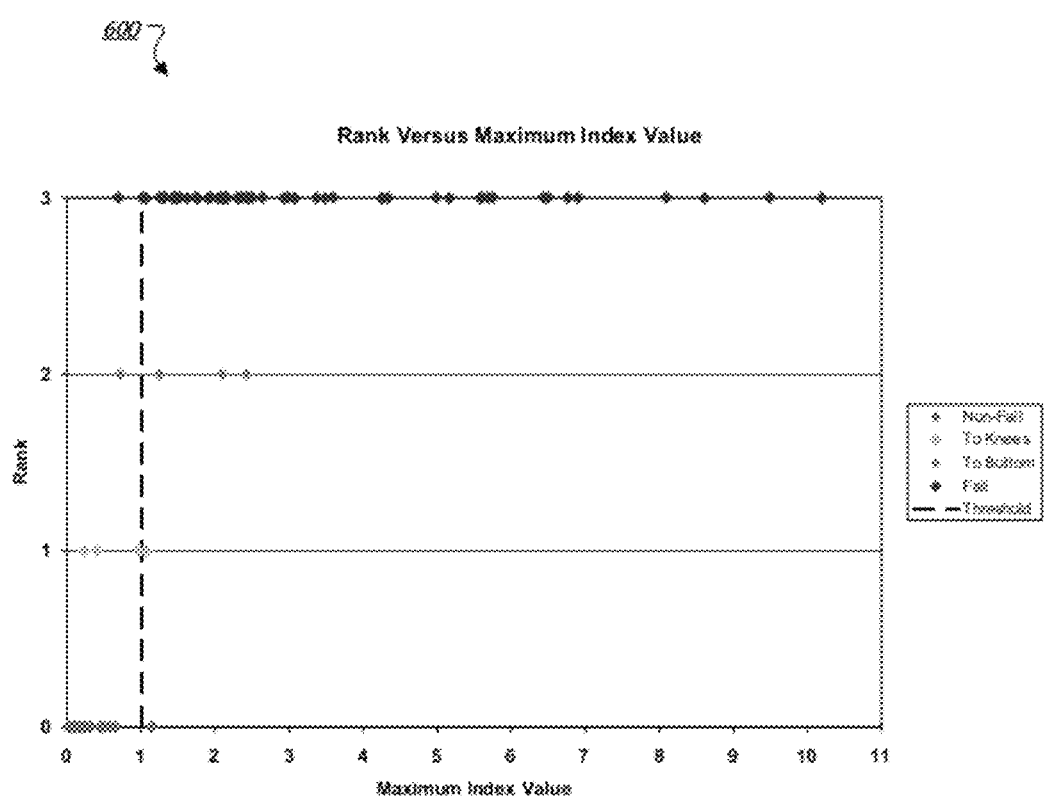
FIG. 6 is a graph of ranked activities versus index values.

Next, scores for each activity were computed and plotted together with the accelerometer waveforms over the time windows for analysis. The behaviors of the scores as a function of time were examined on these plots to evaluate and to fine-tune the analysis. In order to obtain a threshold value for detecting falls, the peak scores for the fall activities and non-fall activities were plotted, as shown in FIG. 6. The data shown in FIG. 6 is based on a mix of about 30 to 40 subjects and 20 to 25 hours of monitoring. For these data, peak scores ranged from 0.018 to 1.146 for non-falls and from 0.692 to 10.186 for falls. These ranges, however, are not as meaningful as measures of the accuracy or sensitivity of fall detection.

The plot 600 of event rank versus maximum index value shows 23 non-fall events assigned a rank of zero (jumps, hard steps, hits by ball, hits by plastic bat, collisions with another person, stumbles, forward leans placing hands on ground, ball kicks, ball throws, ball hits), five "to knees" events assigned a rank of one, four "to bottom" events assigned a rank of two, and 54 fall events assigned a rank of three (e.g., impacts on the ground with the torso deviating from a vertical orientation), for a total of 86 events. Next, the "to knees," rank-one events were combined with the non-fall, rank-zero events to form a new group of 28 newly-defined "non-fall events," and the "to bottom," rank-two events were combined with the fall, rank-three events to form a new group of 58 newly-defined "fall events." The decision threshold was placed at a Maximum Index Value equal to 1.0 (represented by a vertical dashed black line in FIG. 6), which was chosen so that the number of false negatives (FN) equals the number of false positives (FP), so that the number of detected fall activities equals the actual number of fall activities. At the chosen threshold, there are two false positives (FP=2) and two false negatives (FN=2). Because FP=FN, the total number of detected "falls" is 58−FN+FP=58, which is the correct value, so the detection of the total number of falls is accurate. Also, the true positive fraction (TPF)=56/58 or 97%, suggests very good performance.

Example 2

Monitoring Activity of a Child with Cerebral Palsy

Figure 7A:
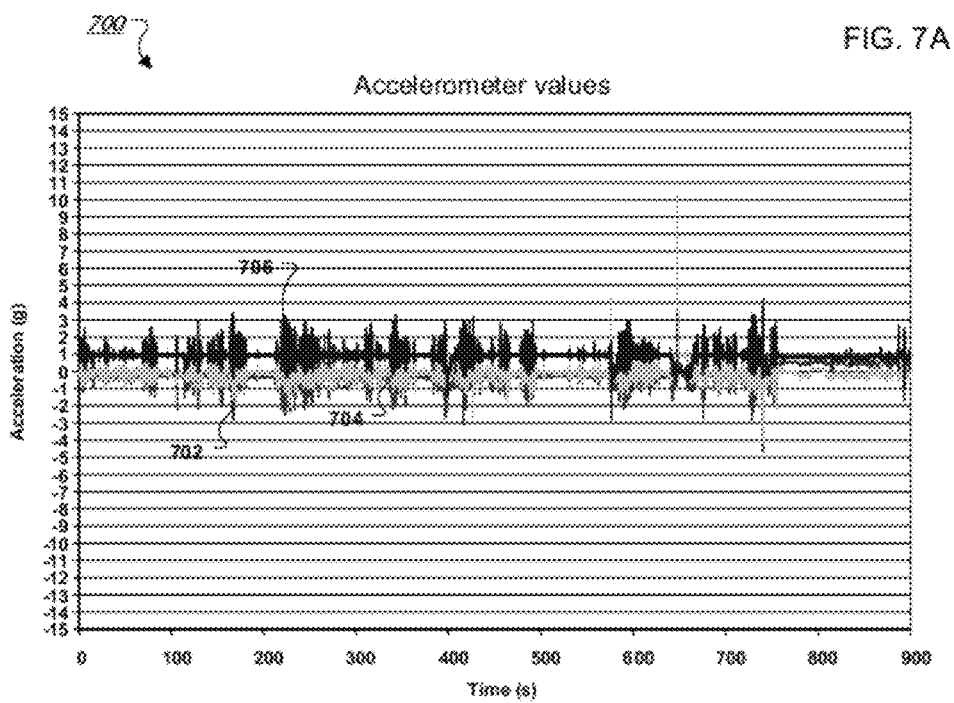
FIG. 7A is a graph of calibrated accelerometer signals.

FIG. 7A shows graph 700, in which calibrated (in g units) accelerometer signals 702 ($A_x$), 704 ($A_y$), and 706 ($A_z$) are plotted for a young boy with cerebral palsy who was wearing an activity monitor 102 during a 15-min. play session. The child was able to stand and walk unaided at different speeds but not able to run. FIG. 7A shows periods when the child was standing relatively quietly (e.g., at around 200 s, after around 500 s) and other periods when the child was walking (e.g., at around 160-170 s, at around 220-260 s). The $A_z$ value is about 1 g, and the $A_x$ and $A_y$ values are about 0 g, reflecting that the child was upright. At about 750 s, the child left the playing area and sat down for the remainder of the recording session. The child leaned forward somewhat in his chair, causing $A_x$ to increase somewhat. Some larger spikes in acceleration are visible, particularly at 576 s, 647 s, and 740 s.

Figure 7B:
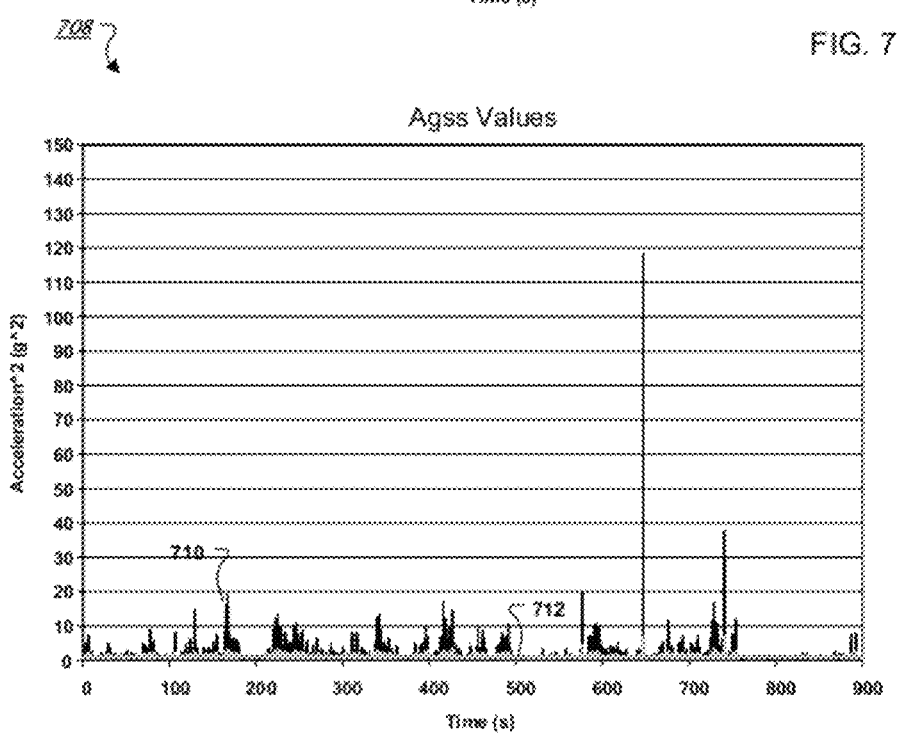
FIG. 7B is a graph of summed-squared, calibrated accelerometer signals.

FIG. 7B shows a graph 708 in which a trace 710 represents a sum of squares of the calibrated $A_x$, $A_y$, and $A_z$ accelerometer signals is plotted. In addition, the sum of squares smoothed over 0.33 s for the accelerometer signals is also plotted as a trace 712. The smoothed sum of squares is intended to be a feature that peaks when a subject strikes the ground during a fall. The smoothing is to accumulate into the height of the peak sequential strikes of multiple parts of the body that may occur during a fall (for example, perhaps first knee, then hands, then hip).

The sum of squares of $A_x$, $A_y$, and $A_z$ accelerometer signals, smoothed or accumulated over a longer time window, is used to evaluate the child's level of activity for that window of time. This value is low when a subject is at rest, increases as the subject walks, and increases more when the subject runs and engages in other vigorous activities.

Figure 8A:
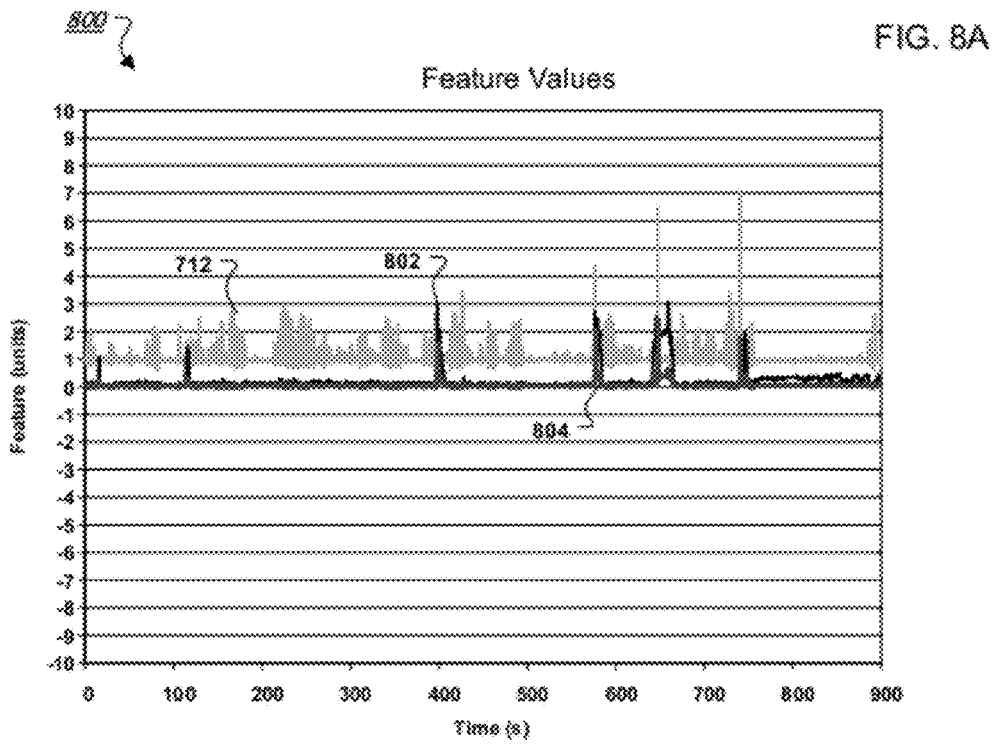
FIG. 8A is a graph of smoothed, summed-squared, calibrated accelerometer signals.

FIG. 8A is a graph 800 in which the trace 712 representing the sum of squares of acceleration is plotted, as well as a trace 802 that represents deviation of the body from vertical, and a score 804 that is a combination of these two features. The score is intended to peak when the subject's body deviates from vertical, as measured by the trace 802, at the same time that the subject experiences large acceleration values (e.g., when the subject falls over and hits the ground), as measured by the trace 712.

Figure 8B:
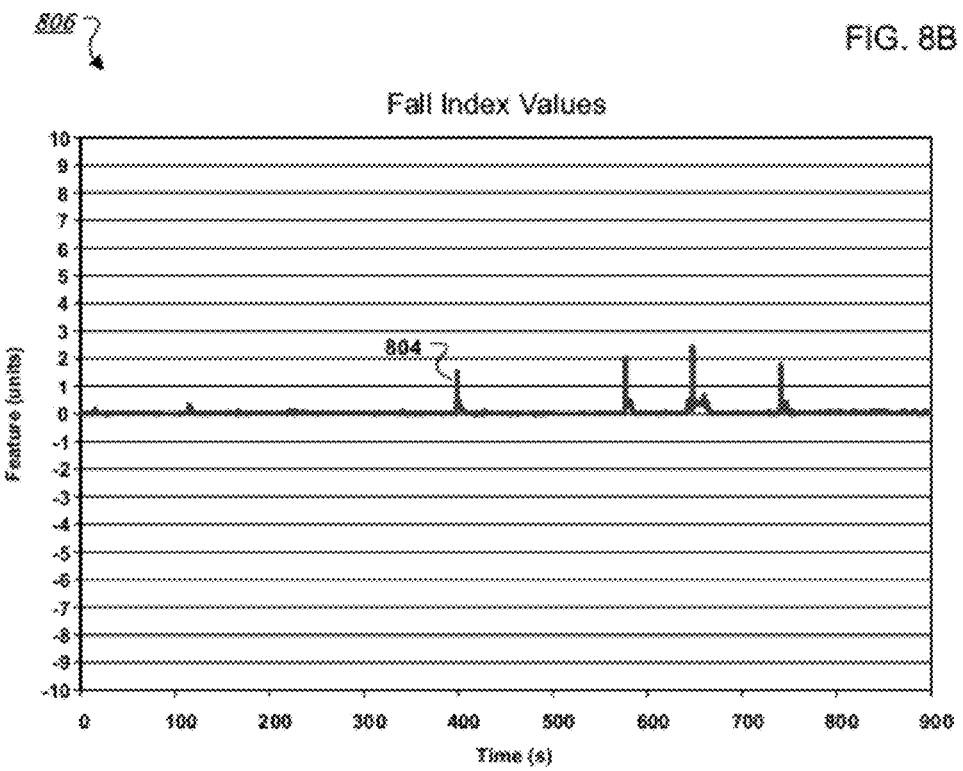
FIG. 8B is a graph representing scores as a function of time.

For clarity, FIG. 8B is a graph 806 that plots the score 804 alone for the signals shown in FIG. 8A. A threshold of 1.0 was established, as discussed in Example 1, to detect a fall event. In FIG. 8B, the score exceeds this threshold value of 1.0 at four times: 399 s, 577 s, 647 s, and 741 s. At these four times, the child fell down. The child did not fall down at any other time. Thus, for this 15-min. recording from a child with cerebral palsy, the automatic fall detection detected all fall events and did not detect false fall events.

There is a smaller peak in the score at time 117 s. At this time, the child leaned forward and placed his hands on the ground, but did not fall. There is an even smaller peak in the score at time 16 s. At this time, the activity monitor 102 was grasped while attached to the child's back, rotated upward by 90 degrees, and then returned it to its previous position. This rotation of the activity monitor 102 was performed in view of the video cameras as a way to synchronize the activity monitor accelerometer recordings and the video recordings.

Figure 9A:
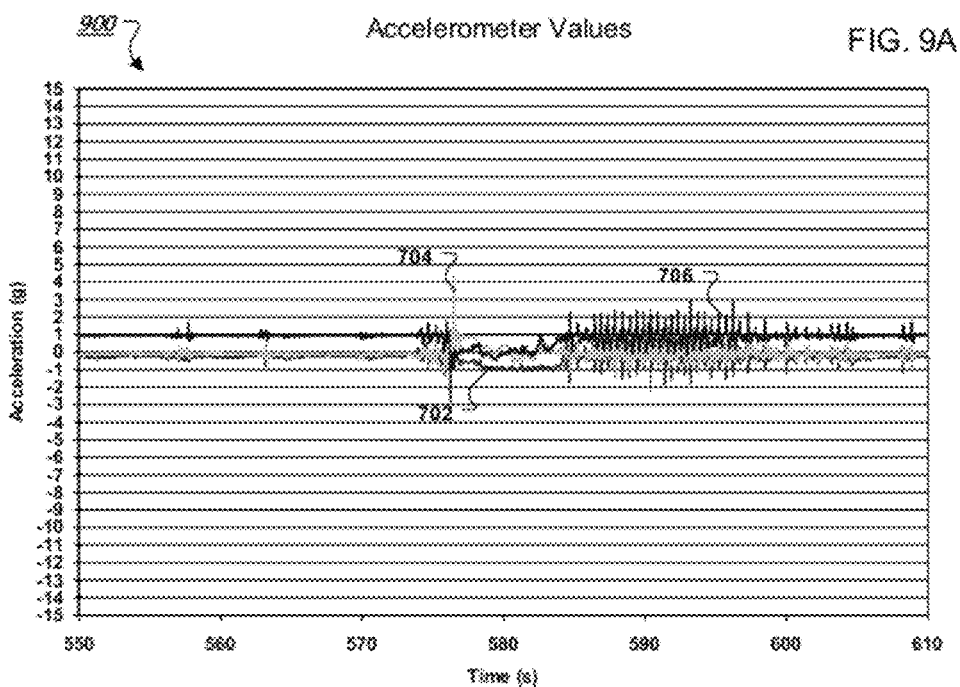
FIG. 9A is an expanded view of a plot of calibrated accelerometer signals for a 60-s window around a fall activity.
Figure 9B:
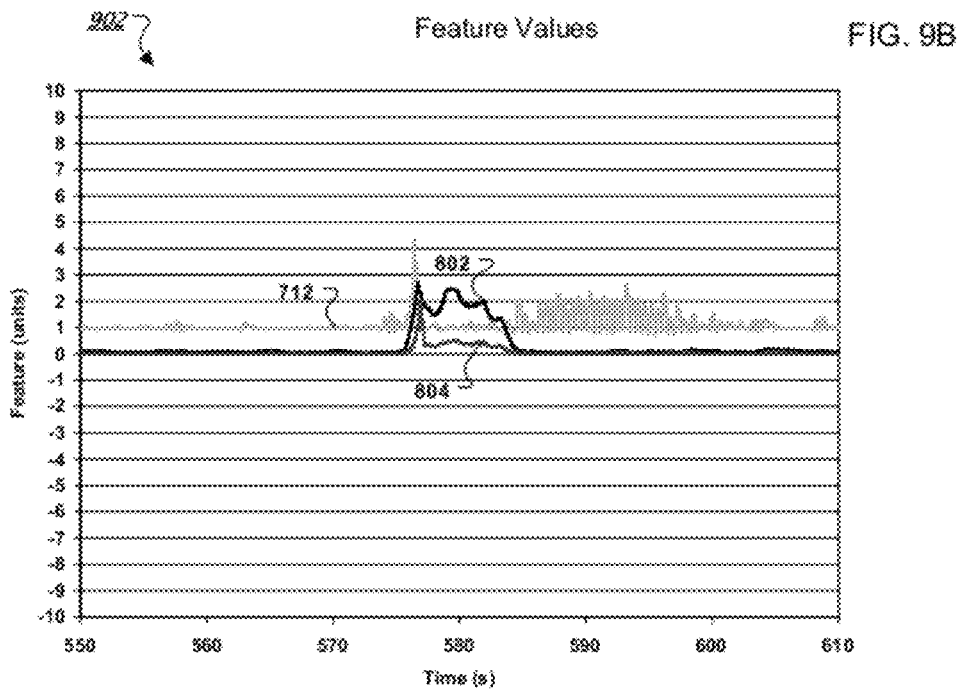
FIG. 9B is an expanded view of a plot of an "impact" feature, "orientation" feature, and a score.

FIG. 9A shows a graph plotting a zoomed-in view 900 of the graph 700 and traces 702, 704, and 706 for a 60-s window around the detected fall at 577 s. FIG. 9B shows a graph plotting traces 712, 802, and 804 for the same time window as FIG. 9A. Both FIG. 9A and FIG. 9B illustrate the time course of the child's standing still (prior to 573 s, becoming unstable (at 573 s), falling (577 s), getting up (585 s), and walking (585 to 599 s).

Other Embodiments

It is to be understood that while the invention has been described in conjunction with the detailed description thereof, the foregoing description is intended to illustrate and not to limit the scope of the invention, which is defined by the scope of the appended claims. Other aspects, advantages, and modifications are within the scope of the following claims.

What is claimed is:

1. A method of activity monitoring, the method comprising:
   delivering data representative of at least one physical activity of an individual from a sensor of an activity monitor associated with the individual to a controller;
   combining the data into at least two intermediate calculations by the controller, wherein a first calculation of the at least two intermediate calculations calculates a first quantity representing an orientation of the individual and a second calculation of the at least two intermediate calculations calculates a second quantity representing a delayed squared norm of an acceleration vector;
   generating by the controller a score from the at least two intermediate calculations by multiplying the first quantity and the second quantity; and
   recording the score as representative of the physical activity in a memory of the controller.

2. The method of claim 1, further comprising:
   recording the data representative of the at least one physical activity in a memory device.

3. The method of claim 1, wherein the controller is part of the activity monitor.

4. The method of claim 1, wherein the controller is part of a computer system in communication with the activity monitor.

5. The method of claim 4, wherein the computer system communicates with the activity monitor through a wireless communication.

6. The method of claim 1, further comprising:
   comparing by the controller the score to a predefined threshold to identify the occurrence of an event; and
   recording the score as representative of the event in the memory of the controller.

7. The method of claim 1, wherein the sensor comprises an accelerometer.

8. The method of claim 6, wherein the threshold is determined by a database of measured data from at least three subjects.

9. The method of claim 6, wherein the event is a fall.

10. The method of claim 1, wherein the the orientation includes a rotational feature.

11. The method of claim 1, further comprising storing squared norms of acceleration vectors over a selected period of time.

12. An apparatus comprising:
   at least one sensor for sensing a physical activity;
   a collector for receiving data representative of the sensed activity, the collector is configured to combine the received data into at least two intermediate calculations, wherein a first calculation of the at least two intermediate calculations calculates a first quantity representing an orientation of the individual and a second calculation of the at least two intermediate calculations calculates a second quantity representing a delayed squared norm of an acceleration vector; and a detector for computing a score from the intermediate calculations by multiplying the first quantity and the second quantity.

13. The apparatus of claim 12, wherein the collector and the detector are components of an activity monitor local to the sensor.

14. The apparatus of claim 12, wherein the detector and the collector are components of a computer system remote to the sensor.

15. The apparatus of claim 14, wherein the computer system communicates with the sensor through a wireless communication.

16. The apparatus of claim 12, further comprising a memory for data storage.

17. The apparatus of claim 12, wherein the sensor includes an accelerometer.

18. The apparatus of claim 12, wherein the orientation includes a rotational feature.

19. The apparatus of claim 12, further comprising a memory for storing squared norms of acceleration vectors over a selected period of time.

20. A computer program product, encoded on a tangible computer-readable medium, operable to cause a data processing apparatus to perform operations comprising:

receiving data representative of at least one physical activity of an individual from an activity monitor associated with the individual;

combining the data into at least two intermediate calculations, wherein a first calculation of the at least two intermediate calculations calculates a first quantity representing an orientation of the individual and a second calculation of the at least two intermediate calculations calculates a second quantity representing a delayed squared norm of an acceleration vector; and generating a score from the at least two intermediate calculations by multiplying the first quantity and the second quantity.

21. The computer program product of claim 20, further comprising:

recording the data representative of the at least one physical activity.

22. The computer program product of claim 20, wherein the data is combined and the score is generated on the activity monitor executing the computer program product.

23. The computer program product of claim 20, wherein the data is combined and the score is generated on a computer system remote to the activity monitor.

24. The computer program product of claim 23, wherein the computer system communicates with the activity monitor through a wireless communication.

25. The computer program product of claim 20, further comprising:

comparing the score to a predefined threshold to identify the occurrence of an event; and recording the score as representative of the event.

26. The computer program product of claim 20, wherein the data is received from at least one sensor comprising an accelerometer.

27. The computer program product of claim 25, wherein the threshold is determined by a database of measured data from at least three subjects.

28. The computer program product of claim 25, wherein the event is a fall.

29. The computer program product of claim 20, wherein the orientation includes a rotational feature.

30. The computer program product of claim 20, wherein the operations further comprise storing squared norms of acceleration vectors over a selected period of time.

31. The method of claim 11, further comprising smoothing the squared norms of the acceleration vectors over the selected period of time.

32. The apparatus of claim 19, wherein the memory also stores smoothed squared norms of the acceleration vectors over the selected period of time.

33. The computer program product of claim 30, wherein the operations further comprise smoothing the squared norms of the acceleration vectors over the selected period of time.

* * * * *

UNITED STATES PATENT AND TRADEMARK OFFICE
CERTIFICATE OF CORRECTION

| | | |
|---|---|---|
| PATENT NO. | : 8,152,745 B2 | Page 1 of 1 |
| APPLICATION NO. | : 12/392606 | |
| DATED | : April 10, 2012 | |
| INVENTOR(S) | : Warren D. Smith and Anita Bagley | |

It is certified that error appears in the above-identified patent and that said Letters Patent is hereby corrected as shown below:

Column 16, Line 55, In Claim 10, delete "the the" and insert -- the --

Signed and Sealed this
Twenty-ninth Day of May, 2012

David J. Kappos
*Director of the United States Patent and Trademark Office*